United States Patent
Sun et al.

(10) Patent No.: US 8,535,225 B2
(45) Date of Patent: Sep. 17, 2013

(54) INTEGRATED COLLIGATION EVALUATING DEVICE FOR HUMAN BODY ENGINERY INDEXES

(75) Inventors: Yin-ing Sun, Guangdong (CN); Zhiming Yao, Guangdong (CN); Tao Han, Guangdong (CN); Xianjun Yang, Guangdong (CN); Xu Zhou, Guangdong (CN)

(73) Assignee: Shenzhen Good Family Enterprise Co., Ltd., Shenzhen, Guangdong (CN)

( * ) Notice: Subject to any disclaimer, the term of this patent is extended or adjusted under 35 U.S.C. 154(b) by 597 days.

(21) Appl. No.: 12/734,248

(22) PCT Filed: Sep. 10, 2008

(86) PCT No.: PCT/CN2008/001603
§ 371 (c)(1),
(2), (4) Date: Apr. 19, 2010

(87) PCT Pub. No.: WO2009/033372
PCT Pub. Date: Mar. 19, 2009

(65) Prior Publication Data
US 2011/0166429 A1     Jul. 7, 2011

(30) Foreign Application Priority Data
Sep. 15, 2007   (CN) .......................... 2007 1 0132390

(51) Int. Cl.
*A61B 5/00*    (2006.01)
(52) U.S. Cl.
USPC ............................ 600/301; 600/300; 128/920
(58) Field of Classification Search
USPC .................................................. 600/300–301
See application file for complete search history.

(56) References Cited

U.S. PATENT DOCUMENTS

| | | | |
|---|---|---|---|
| 6,080,106 A * | 6/2000 | Lloyd et al. | 600/300 |
| 6,403,897 B1 * | 6/2002 | Bluth et al. | 177/144 |
| 6,692,436 B1 * | 2/2004 | Bluth et al. | 600/300 |
| 7,988,627 B2 * | 8/2011 | Bagan | 600/300 |
| 8,083,676 B2 * | 12/2011 | Halliday | 600/301 |
| 2004/0260156 A1 * | 12/2004 | David et al. | 600/300 |
| 2005/0101884 A1 * | 5/2005 | Weeks et al. | 600/587 |
| 2005/0113650 A1 * | 5/2005 | Pacione et al. | 600/300 |
| 2005/0115561 A1 * | 6/2005 | Stahmann et al. | 128/200.24 |
| 2006/0023197 A1 * | 2/2006 | Joel | 355/77 |
| 2007/0043290 A1 * | 2/2007 | Goepp et al. | 600/437 |
| 2008/0083416 A1 * | 4/2008 | Xia et al. | 132/200 |

(Continued)

*Primary Examiner* — Bill Thomson
*Assistant Examiner* — Bobby Soriano
(74) *Attorney, Agent, or Firm* — Raymond Y. Chan; David and Raymond Patent Firm

(57) ABSTRACT

An integrated colligation evaluating device for human body enginery indexes and the working method thereof. The device includes an equipment case (1) provided with a plurality of measuring sensors. A circuit board (13) which is electrically connected with a power source (2) is arranged in the equipment case (1). The circuit board (13) has a plurality of signal processing modules which are electrically connected with a CPU controller (14). Multiple measuring sensors can respectively transfer the human body plural enginery index signals to electrical signals, which are subsequently processed and analyzed by the signal processing modules. The processed electric signals are transmitted to the CPU controller (14) for analyzing and colligation evaluating, or displaying by a terminal displayer (6), or transmitting the human body plural enginery indexes and the human body healthy evaluation results to a master computer for preserving and processing through data transfer interfaces (15), forming and printing reports. The working method includes receiving and processing the human body plural enginery index signals, and conducting colligation evaluating.

3 Claims, 4 Drawing Sheets

(56) References Cited

U.S. PATENT DOCUMENTS

2008/0132383 A1* 6/2008 Einav et al. ................ 482/8
2009/0012655 A1* 1/2009 Kienman et al. ............. 700/300
2009/0203972 A1* 8/2009 Heneghan et al. ........... 600/301

* cited by examiner

INTEGRATED COLLIGATION EVALUATING DEVICE FOR HUMAN BODY ENGINERY INDEXES

BACKGROUND OF THE PRESENT INVENTION

1. Field of Invention

The present invention relates to a medical apparatus, and more particularly to a medical apparatus monitoring a plurality of human physiology index and evaluating human health status, particularly an integrated colligation evaluating device for human physiology indexes.

2. Description of Related Arts

There are various human physiology index testing equipment with various structures. Such equipment generally comprises an equipment case, a power disposed in the equipment case, measuring modules electrically connected with the power and disposed on a circuit board, a CPU controller electrically connected with the power and the measuring module, a terminal display electrically connected with the CPU controller, a keyboard electrically connected with the CPU controller. The measuring module generally comprises a blood pressure measuring module electrically connected with a power supply, a heart rate measuring module electrically connected with the power supply, a blood oxygen content measuring module electrically connected with the power supply and a breath measuring module electrically connected with the power supply. The blood pressure measuring module, the heart rate measuring module, the blood oxygen content measuring module, and the breath measuring module are disposed on different circuit boards respectively, each of which has a CPU controller disposed thereon. Each module collects data by respective sensor, processes the data by respective CPU controller and transmits the processed data to a main CPU controller to realize the human-computer interaction and the display function.

As the human physiology index varies from person to person, even for the same person, his healthy status varies from time to time. Hence, generally, the healthy status needs to be measured and analyzed in a real time manner to provide an accurate evaluation. According to the search of the Information Retrieval Center of the National Intellectual Property Office in China, the most similar current technology is published in a Chinese patent application No. CN 1723839A filed on Jul. 21, 2005, entitled "Method and Device for Testing Health-Index of Individualized and Three-D Type". This invention relates to a method for testing health-index individually and three-D and device thereof, which monitors the change of a plurality of physiology data in different psychology and emotion statuses to test personal comprehensive health status and healthy capacity. In this invention, take the numerical value of a plurality of physiology signals of the subjects in silent status as the base line value, and then affect the psychology and emotion to compare and analyze the change of the plurality of physiology data in order to analyze the individual and three-D healthy status and capacity of the subjects.

The defective of this invention is that the testing procedure needs to affect the psychology and emotion of the subjects and could not test the personal comprehensive health status merely according to a plurality of human physiology index, that means it could not measure a plurality of human physiology index in a real time manner, analyze human health status with comprehensive human physiology index, comprehensively evaluate the human health status and give targeted exercise suggestions. Hence, it is inconvenient for the users to timely obtain their healthy status.

SUMMARY OF THE PRESENT INVENTION

An object of the present invention is to provide an integrated and convenient human physiology index evaluating device for evaluating the body healthy status according to the real time testing result, which overcomes the defects of the current human physiology index testing equipment mentioned above.

Additional advantages and features of the invention will become apparent from the description which follows, and may be realized by means of the instrumentalities and combinations particular point out in the appended claims.

In order to accomplish the object mentioned above, the present invention provides an integrated human physiology index evaluating device comprising a container having a plurality of sensors. The container having the plurality of sensors is an equipment case. The equipment case has a sonar range measuring sensor and an infrared temperature measuring sensor disposed therein, both of which could be extended out and retracted back. The equipment case has a terminal display in an upper portion of the front side thereof, a keyboard disposed under the terminal display, and a heart rate measuring sensor disposed under the keyboard. The equipment case has a body composition testing sensor, an electronic weight measuring sensor and a balanced capacity measuring sensor provided at a lower portion of the front side thereof. The equipment case has a blood pressure measuring sensor provided at an upper portion of the right side thereof. The equipment case has a hand-grip measuring sensor provided at an upper portion of the left side thereof; wherein the equipment case has an ultrasonic bone density measuring sensor provided at the back side thereof.

The heart rate measuring sensor comprises two pairs of electrodes, and the body composition testing sensor comprises four pairs of electrodes including the two pairs of electrodes of the heart rate measuring sensor and other two pairs of electrodes inserted into the electronic weight measuring sensor, wherein the electronic weight measuring sensor is provided above the balanced capacity measuring sensor.

The equipment case comprises a human physiology index signal conditioning circuit disposed therein, which further comprises a sensor component, a data processing component and an input-output component electrically connected with each other. The sensor component comprises a plurality of measuring sensors. The data processing component comprises a circuit board electrically connected with a power supply, wherein the circuit board has a CPU controller, a plurality of signal processing modules and a data transmission interface disposed thereon, wherein the plurality of signal processing modules are electrically connected with the CPU controller and are electrically connected to the plurality of measuring sensors respectively. The input-output component comprises a terminal display and a keyboard electrically connected with the CPU controller.

The measuring sensors convert a plurality of human physiology index signals into electrical signals respectively, processed and analyzed in the plurality of signal processing modules respectively, which further transmit processed electrical signals to the CPU controller for analyzing and evaluating or to the terminal display for displaying or to the data transmission interface for transmitting the human physiology index and evaluating results to an upper monitor for storing, processing, generating and printing a report.

According to the present invention, the plurality of measuring sensors comprises the blood pressure measuring sensor with a model number of BP20X03; the sonar range measuring sensor with a model number SA03009; the infrared temperature measuring sensor with a model number SS0401C/F; the heart rate measuring sensor and the body composition testing sensor both having the electrodes with a model number of BIAHR1.1; the electrical weight measuring sensor and the balanced capacity measuring sensor, both of which are one-dimensional force sensors with a model number of IIM204; the ultrasonic bone density measuring sensor with a GD-V-2 probe of 1 MHz; and the hand-grip measuring sensor with a model number of SWS80.

The CPU controller comprises five CPU controllers with a model number of MSP430F149, including one CPU controller controlling the display, the keyboard, the analyzing and evaluating and other four CPU controller processing and analyzing the plurality of human physiology index signals, wherein each CPU controller has A/D convertor for analog-digital converting.

The blood pressure measuring sensor and the body composition testing sensor can be collapsed in the equipment case. The sonar range measuring sensor and the infrared temperature measuring sensor is arranged to be extended out from the equipment case and retracted back to the equipment case. The electronic weight measuring sensor and the balanced capacity measuring sensor can be shared for usage and can be collapsed in the equipment case.

The plurality of signal processing modules comprises a blood pressure signal processing module, a sonar signal processing module, an infrared signal processing module, a heart rate signal processing module, a body composition processing module, an electrical weight processing module, an balanced capacity processing module, a ultrasonic signal processing module, and a hand-grip signal processing module.

The present invention also provides an evaluating method of the integrated human physiology index evaluating device, including receiving, processing and evaluating a plurality of body physiology index signals, which further comprises the steps of:

setting configuration parameter of the CPU controllers and setting the initialization and self-checking of the CPU controllers;

inputting physical characteristic parameter and determining whether the device has relative information, if not, re-inputting relative information, if so, acquiring electrical signals detected in the plurality of measuring sensors in turn;

initially processing and analyzing a plurality of human physiology index signals to acquire a plurality of human physiology index, and evaluating the plurality of human physiology index and real-time showing health status of human, subsequently providing relative suggestions; and storing the plurality of human physiology index into a database and transmitting the plurality of human physiology index to an upper monitor to form an individual data curve or group data curve finally.

The advantages of the present invention are listed as follows.

Firstly, the defective of the published prior art "method and device for testing health-index of individualized and three-D type" is that the testing procedure needs to affect the psychology and emotion of the subjects and could not test the personal comprehensive health status merely according to a plurality of human physiology index, that means it could not measure a plurality of human physiology index in a real time manner, analyze human health status with comprehensive human physiology index, comprehensively evaluate the human health status and give targeted exercise suggestions. Hence, it is inconvenient for the users to obtain their healthy status.

The present invention provides an integrated human physiology index evaluating device which comprises a container having a plurality of sensors. The container having the plurality of sensors is an equipment case. The equipment case comprises a human physiology index signal conditioning circuit disposed therein, which further comprises a sensor component, a data processing component and an input-output component electrically connected with each other. The sensor component comprises a plurality of measuring sensors. The data processing component comprises a circuit board electrically connected with a power supply, wherein the circuit board has a CPU controller, a plurality of signal processing modules and a data transmission interface disposed therein, wherein the plurality of signal processing modules are electrically connected with the CPU controller and are electrically connected to the plurality of measuring sensors respectively. The input-output component comprises a terminal display and a keyboard electrically connected with the CPU controller.

The measuring sensors convert a plurality of human physiology index signals into electrical signals respectively, processed and analyzed in the plurality of signal processing modules respectively, which further transmit processed electrical signals to the CPU controller for analyzing and evaluating or to the terminal display for displaying or to the data transmission interface for transmitting the human physiology index and evaluating results to an upper monitor for storing, processing, generating and printing a report.

In the present invention, more than one human physiology index testing equipment with different functions are integrated to provide a more efficient and rational structure, which not only reduces the total manufacturing cost, but also realizes the integration and improvement of the function, in which each index could be effectively analyzed and comprehensively evaluated without the reduction of testing capacity of each index.

Secondly, the evaluating method of the integrated human physiology index evaluating device according to the present invention comprises receiving, processing and evaluating a plurality of body physiology index signals, which further comprises the steps of:

setting configuration parameter of the CPU controllers and setting the initialization and self-checking of the CPU controllers;

inputting physical characteristic parameter and determining whether the device has relative information, if not, re-inputting relative information, if so, acquiring electrical signals detected in the plurality of measuring sensors in turn;

initially processing and analyzing a plurality of human physiology index signals to acquire a plurality of human physiology index, and evaluating the plurality of human physiology index and real-time showing health status of human, subsequently providing relative suggestions; and storing the plurality of human physiology index into a database and transmitting the plurality of human physiology index to an upper monitor to form an individual data curve or group data curve finally.

The comprehensively evaluating program of the method is stored in the CPU controller MSP430F149 disposed on the circuit board. That makes the device of the present invention has intelligent function and provides an improvement to the modularization and work speed of the program in the upper monitor.

The present invention further perfects the conventional human physiology index testing equipment that it could not only measure and analyze a plurality of human physiology index, but also integrate the plurality of human physiology index to comprehensively evaluate the healthy status of the user. As a result, most people could timely and efficiently know their self-condition and obtain the guidance and instruction from the healthy and medical experts.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
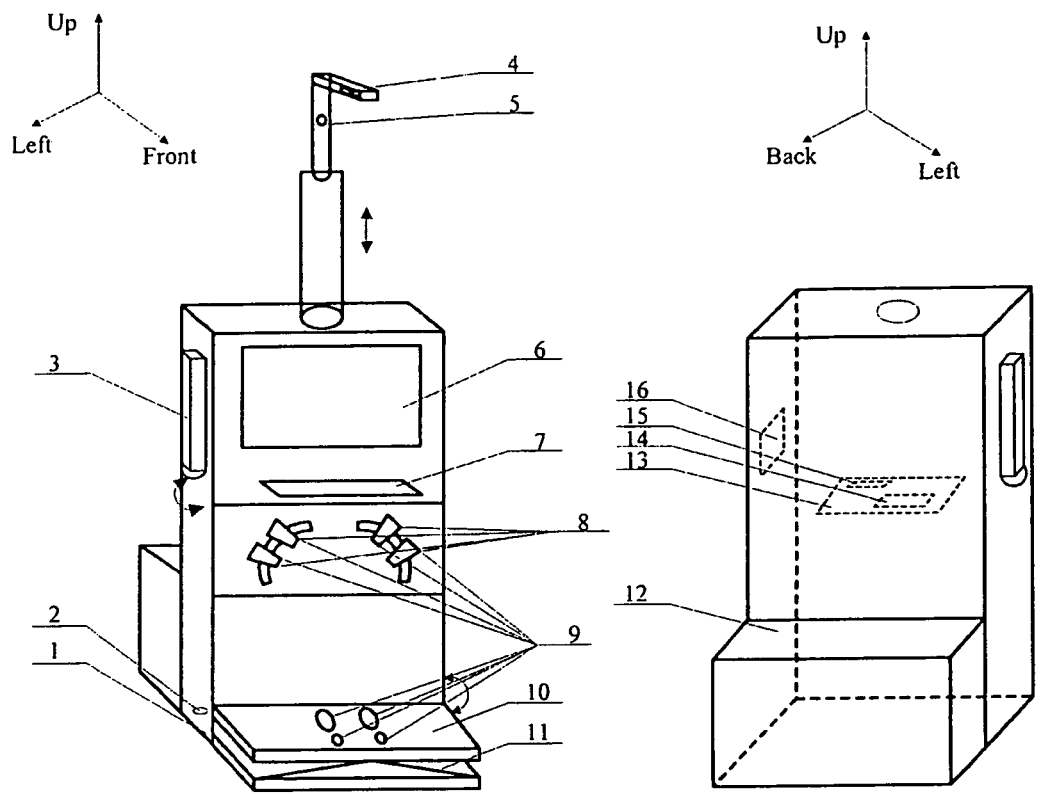
FIG. 1 is a structural perspective view of the present invention.

Referring to the drawings, the embodiments of the present invention are further described as follows.

FIG. 1 is a structural perspective view illustrating the present invention, which comprises an equipment case 1, a power supply 2, a blood pressure measuring sensor 3, a sonar range measuring sensor 4, an infrared temperature measuring sensor 5, a terminal display 6, a keyboard 7, a heart rate measuring sensor 8, a body composition testing sensor 9, an electronic weight measuring sensor 10, a balanced capacity measuring sensor 11, an ultrasonic bone density measuring sensor 12, a circuit board 13, a CPU controller 14, a data transmission interface 15, and a hand-grip measuring sensor 16.

Figure 2:
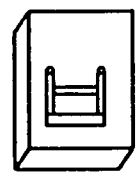
FIG. 2 is an exploded view of the hand-grip measuring sensor of the present invention.

FIG. 2 is an exploded view of the hand-grip measuring sensor. In FIG. 2, the hand-grip measuring sensor converts the force strength of the hand of the user into electrical signal and transmits the electrical signal to a human physiology index signal conditioning circuit for preliminary processing.

Figure 3:
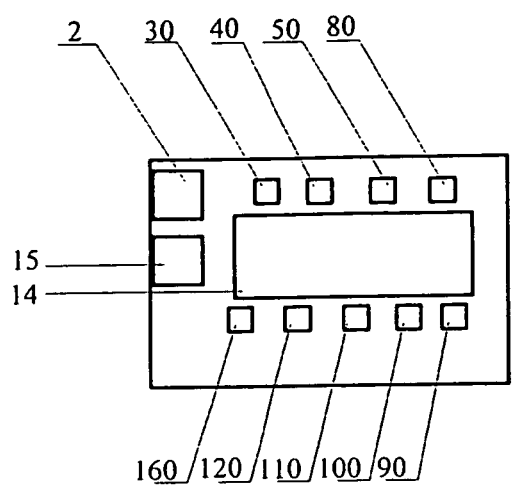
FIG. 3 is a circuit diagram of the circuit board of the present invention.

FIG. 3 is a circuit diagram of the present invention, which comprises the power supply 2, the CPU controller 14, the data transmission interface 15, a blood pressure signal processing module 30, a sonar signal processing module 40, an infrared signal processing module 50, a heart rate signal processing module 80, a body composition processing module 90, an electrical weight processing module 100, an balanced capacity processing module 110, an ultrasonic signal processing module 120, and a hand-grip signal processing module 160.

Figure 4:
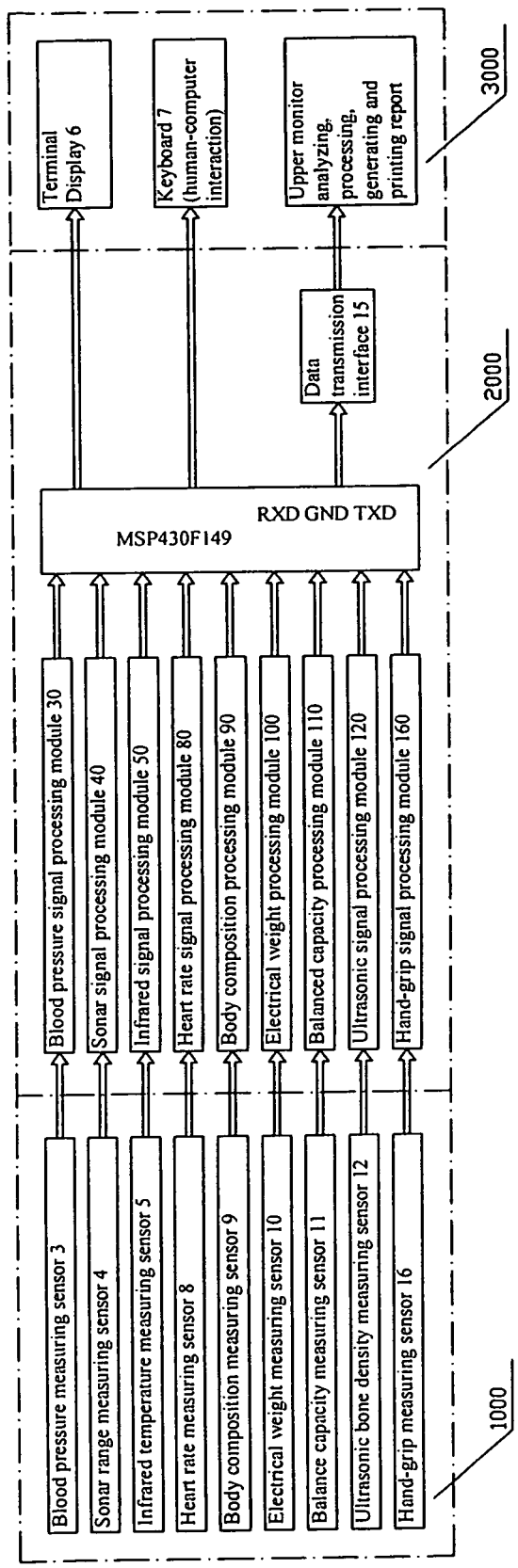
FIG. 4 is a schematic diagram of the circuit of the present invention.

FIG. 4 is a schematic diagram of the circuit of the present invention, which comprises a sensor component 1000, a data processing component 2000, an input-output component 3000, wherein the sensor component 1000 is electrically connected with a plurality of signal processing modules of the data processing component 2000 and the data processing component 2000 is electrically connected with the input-output component 3000 through the data transmission interface 15. In FIG. 4, the component 6 is a terminal display and the component 7 is a keyboard for human interface. The sensor component 1000 comprises the blood pressure measuring sensor 3, the sonar range measuring sensor 4, the infrared temperature measuring sensor 5, the heart rate measuring sensor 8, the body composition testing sensor 9, the electrical weight measuring sensor 10, the balanced capacity measuring sensor 11, the ultrasonic bone density measuring sensor 12, and the hand-grip measuring sensor 16.

The data processing component 2000 comprises the CPU controller 14 MSP430F149, a plurality of signal processing modules electrically connected with the CPU controller 14, and the data transmission interface 15. The plurality of signal processing modules receive relative body data, process and analyze the received data, wherein the plurality of signal processing modules includes the blood pressure signal processing module 30, the sonar signal processing module 40, the infrared signal processing module 50, the heart rate signal processing module 80, the body composition processing module 90, the electrical weight processing module 100, the balanced capacity processing module 110, the ultrasonic signal processing module 120, and the hand-grip signal processing module 160.

The plurality of measuring sensors are electrically connected with the plurality of signal processing modules respectively to convert the plurality of human physiology index signals into electrical signals, and to process and analyze the electrical signals.

The input-output component 3000 comprises the terminal display 6 and the keyboard 7, both of which are electrically connected with the CPU controller MSP430F149 to display a plurality of human physiology indexes and healthy evaluating results, to realize human-computer interaction, and to transmit a plurality of human physiology indexes processed in the data processing component 2 to an upper monitor with a report printed.

The plurality of measuring sensors convert a plurality of human physiology index signals into electrical signals respectively, processed and analyzed in the plurality of signal processing modules respectively, which further transmits processed electrical signals to the CPU controller MSP430F149 for analyzing and evaluating. The body healthy evaluating result is displayed on the terminal display 6 electrically connected with the CPU controller MSP430F149. The keyboard 7 is electrically connected with the CPU controller MSP430F149 to realize human-computer interaction. The data transmission interface 15 is electrically connected with the CPU controller MSP430F149 to transmit the evaluating result to the upper monitor for storing, processing, generating and printing report.

Figure 5:
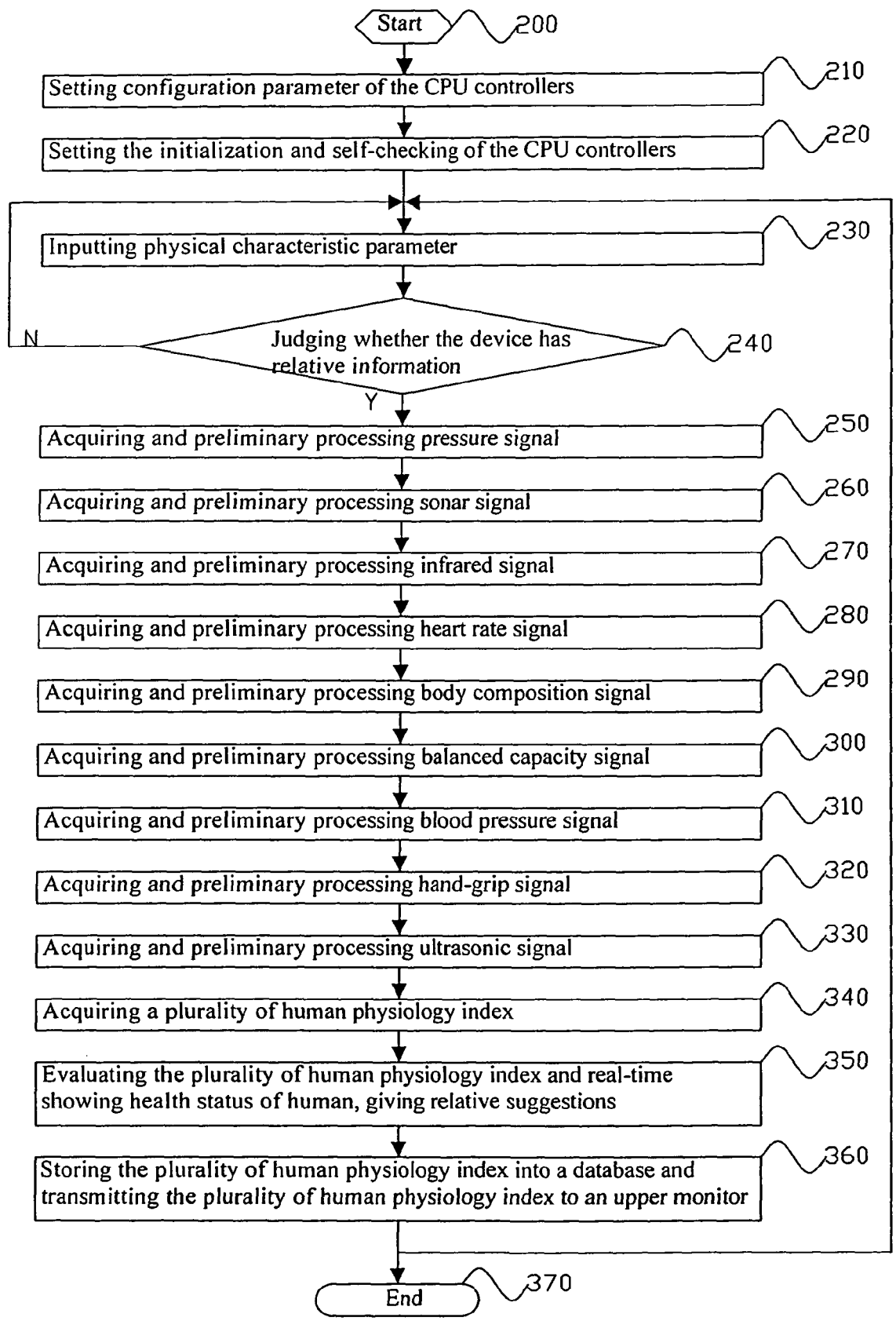
FIG. 5 is a flow chart showing the steps of the present invention.

FIG. 5 is a flow chart showing the steps of the present invention, wherein the steps comprises: (step 200) powering up and staring the integrated human physiology index evaluating device; (step 210) setting configuration parameter of the CPU controllers; (step 220) setting the initialization and self-checking of the CPU controllers; (step 230) inputting physical characteristic parameter; (step 240) determining whether the device has relative information; if not, performing step 230: re-inputting relative information; if so, performing step 250: acquiring and preliminary processing pressure signal; (step 260) acquiring and preliminary processing sonar signal; (step 270) acquiring and preliminary processing infrared signal; (step 280) acquiring and preliminary processing heart rate signal; (step 290) acquiring and preliminary processing body composition signal; (step 300) acquiring and preliminary processing balanced capacity signal; (step 310) acquiring and preliminary processing blood pressure signal; (step 320) acquiring and preliminary processing hand-grip signal; (step 330) acquiring and preliminary processing ultrasonic signal; (step 340) analyzing a plurality of human physiology index signals acquired to acquire a plurality of human physiology index; (step 350) evaluating the plurality of human physiology index and real-time showing health status of human, subsequently providing relative suggestions; (step 360) storing the plurality of human physiology indexes into a database and transmitting the plurality of human physiology indexes to an upper monitor to form an individual data curve or group data curve finally; if there is a new user, repeating the above mentioned steps; if not, performing step 370: turning off the device and cutting off the electricity to finish the measuring, analyzing and evaluating procedure.

In an embodiment, an integrated human physiology index evaluating device comprises a container having a plurality of sensors, wherein the container having the plurality of sensors is the equipment case 1. The equipment case 1 has the sonar range measuring sensor 4 and the infrared temperature measuring sensor 5 disposed therein, both of which could be extended out and retracted back. The equipment case 1 has the terminal display 6 in an upper portion of the front side thereof, the keyboard 7 provided under the terminal display 6, and the heart rate measuring sensor 8 provided under the keyboard 7. The equipment case 1 has the body composition testing sensor 9, the electronic weight measuring sensor 10 and the balanced capacity measuring sensor 11 provided at a lower portion of the front side thereof. The equipment case 1 has the blood pressure measuring sensor 3 provided at an upper portion of the right side thereof. The equipment case 1 has the hand-grip measuring sensor 16 provided at an upper portion of the left side thereof. The equipment case 1 has the ultrasonic bone density measuring sensor 12 provided at the back side thereof.

The heart rate measuring sensor 8 comprises two pairs of electrodes, and the body composition testing sensor 9 comprises four pairs of electrodes including the two pairs of electrodes of the heart rate measuring sensor 8 and other two pairs of electrodes inserted into the electronic weight measuring sensor 10, wherein the electronic weight measuring sensor 10 is provided above the balanced capacity measuring sensor 11.

The equipment case 1 comprises a human physiology index signal conditioning circuit disposed therein, which further comprises the sensor component 1000, the data processing component 2000 and the input-output component 3000 electrically connected with each other. The sensor component 1000 comprises the plurality of measuring sensors. The data processing component 2000 comprises the circuit board 13 electrically connected with the power supply 2, wherein the circuit board 13 has the CPU controller 14, the plurality of signal processing modules and the data transmission interface 15 provided thereon, wherein the plurality of signal processing modules are electrically connected with the CPU controller 14 and are electrically connected to the plurality of measuring sensors respectively. The input-output component 3000 comprises the terminal display 6 and the keyboard 7 electrically connected with the CPU controller 14.

The plurality of measuring sensors convert the plurality of human physiology index signals into electrical signals respectively, processed and analyzed in the plurality of signal processing modules respectively, which further transmit processed electrical signals to the CPU controller 14 for analyzing and evaluating or to the terminal display 6 for displaying or to the data transmission interface 15 for transmitting the human physiology index and evaluating results to the upper monitor for storing, processing, generating and printing the report.

The plurality of measuring sensors comprises the blood pressure measuring sensor 3 with a model number of BP20X03; the sonar range measuring sensor 4 with a model number SA03009; the infrared temperature measuring sensor 5 with a model number SS0401C/F; the heart rate measuring sensor 8 and the body composition testing sensor 9 both having the electrodes with a model number of BIAHR1.1; the electrical weight measuring sensor 10 and the balanced capacity measuring sensor 11, both of which are one-dimensional force sensors with a model number of IIM204; the ultrasonic bone density measuring sensor 12 with a GD-V-2 probe of 1 MHz; and the hand-grip measuring sensor 16 with a model number of SWS80.

The CPU controller 14 comprises five CPU controllers with a model number of MSP430F149 including one CPU controller controlling the display, the keyboard, the analyzing and evaluating and other four CPU controller processing and analyzing the plurality of human physiology index signals, wherein each CPU controller 14 has A/D convertor for analog-digital converting.

The blood pressure measuring sensor 3 and the body composition testing sensor 9 can be collapsed in the equipment case 1. The sonar range measuring sensor 4 and the infrared temperature measuring sensor 5 are arranged to be extended out from the equipment case 1 and retracted back to the equipment case 1. The electronic weight measuring sensor 10 and the balanced capacity measuring sensor 11 can be shared for usage and can be collapsed in the equipment case 1.

The plurality of signal processing modules comprises the blood pressure signal processing module 30, the sonar signal processing module 40, the infrared signal processing module 50, the heart rate signal processing module 80, the body composition processing module 90, the electrical weight processing module 100, the balanced capacity processing module 110, the ultrasonic signal processing module 120, and the hand-grip signal processing module 160.

An evaluating method of the integrated human physiology index evaluating device comprises receiving, processing and evaluating a plurality of body physiology index signals, which further comprises the steps of setting configuration parameter of the CPU controllers and setting the initialization and self-checking of the CPU controllers;

inputting physical characteristic parameter and determining whether the device has relative information, if not, re-inputting relative information, if so, acquiring electrical signals detected in the plurality of measuring sensors in turn;

initially processing and analyzing a plurality of human physiology index signals to acquire a plurality of human physiology index, and evaluating the plurality of human physiology index and showing health status of human in a real time manner, subsequently providing relative suggestions; and storing the plurality of human physiology index into the database and transmitting the plurality of human physiology index to the upper monitor to form the individual data curve or group data curve finally.

After starting the device, the user firstly turns on the power supply 2 and then turns on each measuring sensor into working status in turn. Firstly, input personal information by the keyboard 7, including name, gender, age and so on. Then following the tips, the user stands on the electronic weight measuring sensor 10 disposed on a lower portion of the front side of the integrated human physiology index evaluating device, and the balanced capacity signal of the user could also be acquired by the balanced capacity measuring sensor 11 at the same time. The user has its feet on the body composition testing sensor 9 and its hands holding the heart rate measuring sensor 8, and then adjusts the sonar range measuring sensor 4 and the infrared temperature measuring sensor 5 to a suitable position. After one minute, six body indexes of the user could be collected and displayed on the terminal display 6, wherein the six body indexes are weight, temperature, height, heart rate, body composition and balanced capacity. Then turn on the blood pressure measuring sensor 3 and put the user's arm on a test table with belts adjusted according to the thickness of the arm. After 30 seconds, the diastolic pressure and the systolic pressure of the user will be displayed on the terminal display 6. Then use the hand-grip measuring sensor 16 to acquire the force information of the user and use the ultrasonic bone density measuring sensor 12 to acquire the value of the bone density of the user. Finally, the human physiology index signal conditioning circuit preliminary processes the plurality of human physiology index signals acquired by each measuring sensor mentioned above and transmits the processed plurality of human physiology index signals to the CPU controller 14 for analyzing and evaluating. Then the CPU controller 14 obtains the body healthy status of the user and provides relative suggestions, and the plurality of human physiology indexes and the body healthy evaluating result will be displayed on the terminal display 6 and be transmitted through the data transmission interface 15 for printing.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An integrated human physiology index comprehensive evaluating device, comprising:

an equipment case which comprises a terminal display provided at an upper portion of said equipment case at a front side thereof and a keyboard provided under said terminal display for inputting personal information of a user;

a sensor component for collecting a plurality of human physiology indexes, wherein said sensor component comprises:

a six-body-index sensor for collecting six body indexes of the user at the same time, wherein said six-body-index sensor, which is held by said equipment case, comprises:

an electronic weight measuring sensor provided at a lower portion of said equipment case at a front side thereof for enabling a user standing on said equipment case to measure a weight of the user;

a balanced capacity measuring sensor provided at said equipment case at a position that said electronic weight measuring sensor is provided above said balanced capacity measuring sensor, wherein said balance capacity measuring sensor acquires a balanced capacity signal of the user at the same time when the weight of the user is measured;

a heart rate measuring sensor provided at said equipment case under said keyboard for enabling a hand of the user to hold said heart rate measuring sensor;

a body composition testing sensor which comprising four pairs of electrodes including said two pairs of electrodes of said heart rate measuring sensor and other two pairs of electrodes inserted into said electronic weight measuring sensor;

an infrared temperature measuring sensor for measuring body temperature of the user; and a sonar range measuring sensor, wherein said infrared temperature measuring sensor and said sonar range measuring sensor are retractably provided at said equipment case, such that said infrared temperature measuring sensor and said sonar range measuring sensor are extended out from said equipment case and are adjustable with respect to the user; wherein said six body indexes of the user are collected and displayed on said terminal display in a real time manner, wherein said six body indexes are weight, temperature, height, heart rate, body composition and balanced capacity;

a blood pressure measuring sensor provided at said upper portion of said equipment case at a right side thereof for collecting diastolic pressure and systolic pressure of the user which are displayed on said terminal display;

a hand-grip measuring sensor provided at said upper portion of said equipment case at a left side thereof for acquiring force information of the user when the hand of the user grips at said hand-grip measuring sensor; and a ultrasonic bone density measuring sensor provided at a back side of said equipment case for acquiring value of bone density of the user; and a CPU controller for analyzing and comprehensively evaluating values of human physiology indexes from said sensor component to provide a body healthy evaluating result with respect to the user.

2. The integrated human physiology index comprehensive evaluating device, as recited in claim 1, further comprises a plurality of signal processing modules linked to said CPU controller, wherein said signal processing modules are blood pressure signal processing module linked to said blood pressure measuring sensor, sonar signal processing module linked to said sonar range measuring sensor, infrared signal processing module linked to said infrared temperature measuring sensor, heart rate signal processing module linked to said heart rate measuring sensor, body composition processing module linked to said body composition testing sensor, electrical weight processing module linked to said electronic weight measuring sensor, balanced capacity processing module linked to said balanced capacity measuring sensor, ultrasonic signal processing module linked to said ultrasonic bone density measuring sensor, and hand-grip signal processing module linked to said hand-grip measuring sensor.

3. The integrated human physiology index comprehensive evaluating device, as recited in claim 2, wherein each of said signal processing modules converts human physiology index signals from said corresponding sensor into electrical signals for said CPU controller.

* * * * *